United States Patent
Ebert et al.

(10) Patent No.: US 10,028,506 B2
(45) Date of Patent: Jul. 24, 2018

(54) PLANT STRENGTHENER COMPRISING A TOCOPHEROL AND A BORON COMPOUND

(71) Applicant: COMPO EXPERT GMBH, Münster (DE)

(72) Inventors: Georg Ebert, Potsdam (DE); Christian Jaeger, Münster (DE)

(73) Assignee: COMPO EXPERT GMBH, Münster (DE)

( * ) Notice: Subject to any disclaimer, the term of this patent is extended or adjusted under 35 U.S.C. 154(b) by 0 days.

(21) Appl. No.: 14/891,549

(22) PCT Filed: May 16, 2014

(86) PCT No.: PCT/EP2014/060086
§ 371 (c)(1),
(2) Date: Nov. 16, 2015

(87) PCT Pub. No.: WO2014/184346
PCT Pub. Date: Nov. 20, 2014

(65) Prior Publication Data
US 2016/0088840 A1     Mar. 31, 2016

(30) Foreign Application Priority Data
May 17, 2013   (EP) .................................... 13168252

(51) Int. Cl.
| | | |
|---|---|---|
| A01N 43/16 | (2006.01) | |
| A01N 61/00 | (2006.01) | |
| A01N 25/12 | (2006.01) | |
| A01N 49/00 | (2006.01) | |
| A01N 43/08 | (2006.01) | |
| A01N 25/04 | (2006.01) | |
| C05D 9/02 | (2006.01) | |
| C05G 3/00 | (2006.01) | |

(52) U.S. Cl.
CPC ............. *A01N 43/16* (2013.01); *A01N 25/04* (2013.01); *C05D 9/02* (2013.01); *C05G 3/00* (2013.01)

(58) Field of Classification Search
CPC ........ A01N 43/16; A01N 25/04; A01N 55/08; C05D 9/02; C05G 3/00
See application file for complete search history.

(56) References Cited

U.S. PATENT DOCUMENTS

| | | | |
|---|---|---|---|
| 2008/0200561 A1* | 8/2008 | Wirth ....................... | C05D 9/02 514/772 |
| 2013/0078272 A1* | 3/2013 | Villas-Boas ........... | A61K 36/06 424/195.15 |

FOREIGN PATENT DOCUMENTS

| | | | |
|---|---|---|---|
| CN | 1544397 A | | 11/2004 |
| DE | 4437945 | * | 4/1995 |
| DE | 4437945 A1 | | 4/1995 |
| DE | 19904703 A1 | | 8/2000 |
| SU | 793968 | * | 11/1978 |
| WO | 1989011795 A1 | | 12/1989 |

OTHER PUBLICATIONS

Patent Cooperation Treaty, International Searching Authority, Search Report for PCT/EP2014/060086, 3 pages, dated Jul. 4, 2014.
XP002711775, Database CA [Online], retrieved from STN, Database accession No. 154:63951, 1 page: CN101913948 A, SHI, Chenhua, "Liquid boron fertilizer and preparation method thereof" (2010).

* cited by examiner

*Primary Examiner* — Mina Haghighatian
(74) *Attorney, Agent, or Firm* — Viksnins Harris Padys Malen LLP

(57) ABSTRACT

The present invention relates to a plant strengthener in the form of a formulation comprising tocopherol or a derivative of a tocopherol, and to the use thereof for increasing the tolerance of crop plants to stress events, in particular to chemically induced stress, cold-induced stress, drought-induced stress or light-induced stress.
The plant strengtheners are present in the form of formulations which comprise the following components A, B and C:
a) at least one tocopherol or derivative of a tocopherol (component A);
b) at least one nonionic emulsifier (component B); and
c) at least one water-soluble boron compound (component C),
and, if appropriate,
d) one or more UV absorbers (component D) and
e) one or more organic solvents.

19 Claims, No Drawings

PLANT STRENGTHENER COMPRISING A TOCOPHEROL AND A BORON COMPOUND

RELATED APPLICATIONS

This patent application claims the benefit of EP Patent Application No. 13168252.8 filed May 17, 2013.

The present invention relates to a plant strengthener in the form of a formulation comprising tocopherol or a derivative of a tocopherol, and to the use thereof for increasing the tolerance of crop plants to stress events, in particular to chemically induced stress, cold-induced stress, drought-induced stress or light-induced stress.

Besides being threatened by diseases or pests, crop plants increasingly also suffer from what are known as abiotic stress factors, the most important of which being extreme temperatures (cold-induced stress as the result of frost, drought in the case of high temperatures), high degree of solar radiation (light-induced stress as the result of UV components in the sunlight) and water deficiency. Frost, especially in spring when plant growth commences, can likewise cause considerable yield losses or quality losses as the result of the plant tissue freezing. Intense solar radiation, in particular during fruit maturation of various types of fruit, results in economically important damage on the fruits.

All abiotic stress factors cause not only the direct harmful events (for example development of ice in the tissue in the case of frost), but also what is known as an oxidative stress reaction of the plant. The development of reactive oxygen species (ROS) and free radicals of chemicals in the plant tissue, which, in the form of chain reactions, attack components of the plant cell and destroy them by means of oxidation, is considered to be the immediate consequence of the action of stress. The cell membranes such as, for example, the thylakoid membrane of the chloroplasts, are especially sensitive. One of the consequences is that the photosynthetic performance is reduced, and pronounced yield losses ensue.

A further problem are stress events which are caused by environmental toxins such as ozone or which are the result of the application of crop protectants such as fungicides, insecticides, bactericides, herbicides, acaricides or growth regulators or from the use of certain fertilizers (chemically induced stress), in particular when such stress events take place together with other abiotic stress events.

As outlined already, all of the abovementioned stress events result in pronounced yield losses. Furthermore, fruits frequently develop necrotic or suberizing patches as the result of such stress events, which means that these fruits are only capable of being marketed to some extent or else can no longer be used for high-grade processing purposes. Also, the storability and shelf life of fruits may be limited as the result of such stress events.

Within the framework of high-level quality and yield assurance, agricultural operations and plant growers therefore take a great interest in protecting the plants from damage caused by abiotic stress factors and toxins by strengthening their intrinsic defense mechanisms or by inhibiting direct effects of noxious substances.

WO 89/11 795 discloses a method for increasing the resistance of plants by using environmentally compatible antioxidants, such as, for example, ascorbic acid or tocopherols. It is assumed that the active principle is that the antioxidants, being what is known as "exo-elicitors", cause a protective response, whereby the resistance to for example plant protectants or environmental toxins is said to improve, thus reducing the degree of toxicity of plant protectants. The abovementioned document describes results which document the immediate participation of antioxidants in stress defense reactions. Here, the protective function is a direction function of the concentration of the antioxidant active substance in the plant cell. The prerequisite for such an active principle, however, is that the antioxidants, for example tocopherols, are taken up efficiently by the plant.

DE 4437945 describes a plant strengthener in the form of a formulation which comprises a compound from among the vitamin E group, for example α-tocopherol, and a surfactant.

DE 19904703 describes the joint application of tocopherol-comprising plant strengtheners together with methoxycinnamic acid or its derivatives for improving the plants tolerance to UV radiation-induced stress. The methoxycinnamic acid (derivatives) are employed together with the tocopherol-comprising plant strengthener in the form of a tank mix.

The protection of plants from the abovementioned stress factors by the means known from the aforementioned prior art is, however, not always satisfactory, in particular when the plants are grown on nutrient-deficient or light soils. It is therefore an object of the present invention to provide formulations which ensure an improved protection of the plants against stress events, in particular abiotic stress (light-induced, drought-induced or cold-induced stress) and/or against stress caused by toxins (chemically induced stress). Moreover, it is intended that the formulation be storage-stable and also easy to handle and that it should ensure a uniform distribution of the constituents in the spray mixture when diluted with water to the desired use concentration.

This object and further objects are solved by the boron-comprising formulations which are described in greater detail hereinbelow.

The present invention therefore relates to plant strengtheners in the form of formulations which comprise the following components A, B and C:

a) at least one tocopherol or derivative of a tocopherol (component A);

b) at least one nonionic emulsifier (component B); and c) at least one water-soluble boron compound (component C).

The formulations according to the invention have a series of advantages. Firstly, they are distinguished by an improved activity in respect of the protection of the treated plants in the event of stress-caused strain. What is achieved is in particular an improved protective activity against damage as the result of water loss or drying-out of the plant, be it as the result of heat, drought or cold events. Moreover, the treatment with the plant strengtheners according to the invention results in an improved fertility, in particular in the case of woody fruiting species and of fruit vegetables, for example an improved fruit set and/or improved fruit development, for example in the case of tomato or bell pepper. Therefore, the treatment with the plant strengtheners according to the invention results in the safeguarding and increasing of the fruit yields. Frequently, the treated plants also display better plant fitness against diseases and pests. The advantages mentioned herein are especially pronounced in the case of intensive farming and/or farming on nutrient-deficient, light soils.

Therefore, another subject matter of the invention is the use of the plant strengtheners according to the invention for increasing the tolerance of crop plants to stress events, in particular to chemically induced stress, cold-induced stress, drought-induced stress or light-induced stress.

Another subject matter of the invention is a method for the treatment of plants, in particular crop plants, in which the plants or their environment are treated with a plant strengthener according to the invention.

The formulations according to the invention comprise, as component A, at least one tocopherol or tocopherol derivative. Tocopherol and its derivatives are understood as meaning the compounds of the vitamin E group, i.e. tocopherols, tocomonoenols, marine tocopherols and tocotrienols and the esters of these compounds, in particular the acetates. Preferred as component A are tocopherols such as α-tocopherol, β-tocopherol, γ-tocopherol and δ-tocopherol and their esters, in particular their acetates. In particular, component A comprises α-tocopherol, specifically the naturally occurring RRR isomer of α-tocopherol or a mixture of α-tocopherol, in particular of the RRR isomer, with one or more compounds of the vitamin E group which differ therefrom, in particular mixtures of α-tocopherol, in particular of the RRR isomer, with one or more compounds of the vitamin E group selected among α-tocopherol, β-tocopherol, γ-tocopherol, δ-tocopherol and their esters, in particular their acetates.

As a rule, the total concentration of component A in formulations according to the invention is from 50 to 500 g/l, in particular from 100 to 400 g/l.

As component B, the formulations according to the invention comprise at least one nonionic surfactant which is preferably selected from among the emulsifiers of the following classes B.1 to B.9 and their mixtures:

B.1 poly-$C_2$-$C_3$-alkoxylated $C_3$-$C_{18}$-alkylphenols, preferably those with a degree of alkoxylation in the range of from 2 to 100, in particular from 3 to 80, specifically from 3 to 50, for example polyethoxylated octylphenol, polyethoxylated nonylphenol or polyethoxylated dodecylphenol;

B.2 poly-$C_2$-$C_3$-alkoxylated $C_{10}$-$C_{22}$-fatty alcohols, in particular poly-$C_2$-$C_3$-alkoxylated $C_{10}$-$C_{22}$-alkanols and poly-$C_2$-$C_3$-alkoxylated $C_{10}$-$C_{22}$-alkenols, in each case with a degree of alkoxylation in the range of from 2 to 100, in particular from 3 to 80, especially from 4 to 50, specifically poly-$C_2$-$C_3$-alkoxylated $C_{14}$-$C_{20}$-alkanols, such as polyethoxylated lauryl alcohol, polyethoxylated myristyl alcohol, polyethoxylated palmityl alcohol, polyethoxylated cetyl alcohol, polyethoxylated cetylstearyl alcohol, polyethoxylated stearyl alcohol and polyethoxylated oleyl alcohol, and the corresponding poly(ethoxy-co-propoxylated) $C_{10}$-$C_{22}$-alkanols and $C_{10}$-$C_{22}$-alkenols;

B.3 poly-$C_2$-$C_3$-alkoxylated $C_{10}$-$C_{22}$-fatty acid esters, in particular polyethoxylated $C_{10}$-$C_{22}$-fatty acid esters, in particular poly-$C_2$-$C_3$-alkoxylated $C_{10}$-$C_{22}$-fatty acid monoglycerides and diglycerides and mixtures of these;

B.4 copolymers of propylene oxide and ethylene oxide, in particular block copolymers, specifically those with a central polypropylene block and two polyethylene oxide blocks, in particular those with a molecular weight in the range of between 1000 and 20 000 Daltons (number average);

B.5 sucroglycerides, also referred to as sugar glycerides, i.e. transesterification products of fatty acid triglycerides, in particular of $C_{10}$-$C_{12}$-fatty acid triglycerides with glucose or sucrose, for example the emulsifier of the E474 type;

B.6 polyethoxylated $C_{10}$-$C_{18}$-fatty acid esters of sorbitan, in particular those with a degree of ethoxylation of from 10 to 50, for example polyoxyethylene(20) sorbitan monolaurate, polyoxyethylene(20) sorbitan monopalmitate, polyoxyethylene(20) sorbitan monooleate, polyoxyethylene(20) sorbitan monostearate and polyoxyethylene(20) sorbitan tristearate;

B.7 polyethoxylated lanolin alcohols (polyethoxylated lanolin), for example polyethoxylated lanolin alcohols with a degree of ethoxylation in the range of from 10 to 100, preferably from 30 to 90, in particular from 40 to 85.

B.8 $C_8$-$C_{16}$-alkylpolyglucosides, also known as APGs, in particular those with a $C_8$-$C_{14}$-alkyl radical and 1 to 5 glucose units, for example octylpolyglycosides, 2-ethylhexylpolyglycosides, decylpolyglycosides, dodecylpolyglycosides and tetradecylpolyglycosides, for example those with 1 to 3 glucose units;

B.9 poly-$C_2$-$C_3$-alkoxylated triglycerides of aliphatic $C_{10}$-$C_{22}$-hydroxycarboxylic acids, for example those with a degree of alkoxylation in the range of from 10 to 100, in particular from 15 to 70, specifically from 20 to 60, in particular polyethoxylated triglycerides of aliphatic $C_{10}$-$C_{22}$-hydroxycarboxylic acids, specifically castor oil ethoxylates, in particular castor oil ethoxylates with a degree of ethoxylation in the range of from 10 to 100, in particular from 15 to 70, specifically from 20 to 60.

The abovementioned poly-$C_2$-$C_3$-alkoxylated emulsifiers are understood as meaning those substances which include at least one polyoxy-$C_2$-$C_4$-alkylene group. The degree of alkoxylation of the poly-$C_2$-$C_3$-alkoxylated emulsifiers describes the mean (number average) number of $C_2$-$C_3$-oxyalkylene groups, i.e. groups of the formula [Z—O] in polyoxy-$C_2$-$C_3$-alkylene groups, which corresponds to the molar number of $C_2$-$C_3$-oxirane per mole of OH groups of the polyalkoxylated compound. In this context, the prefix $C_n$-$C_m$ indicates the possible number of carbon atoms in the molecule or in the radical referred to thereby, i.e. $C_n$-$C_m$-alkyl is a collective term for linear or branched alkyl radicals which may include n to m carbon atoms, i.e. $C_3$-$C_{18}$-alkyl represents the group of the alkyl radicals which include 3 to 18 C atoms, for example propyl, butyl, pentyl, hexyl, heptyl, octyl, nonyl, decyl, undecyl, dodecyl, tridecyl, tetradecyl, hexadecyl, octadecyl, eicosyl, and the branched isomers of the abovementioned radicals. The term $C_{10}$-$C_{22}$-alkanols therefore represents the group of the saturated aliphatic alcohols, in particular of the fatty alcohols, which include 10 to 22 carbon atoms, such as decyl alcohol, lauryl alcohol, myristyl alcohol, cetyl alcohol, stearyl alcohol, eicosanol and behenyl alcohol. The term cetylstearyl alcohol represents a mixture of $C_{16}$/$C_{18}$-fatty alcohols. The term $C_{10}$-$C_{22}$-alkenols therefore represents the group of the unsaturated aliphatic alcohols which include 10 to 22 carbon atoms, such as oleyl alcohol. The term $C_{10}$-$C_{22}$-fatty acid therefore represents the group of the alkanecarboxylic acids and alkenecarboxylic acids, in particular of the native alkanecarboxylic acids, which include 10 to 22 C atoms. The term $C_{10}$-$C_{22}$-hydroxycarboxylic acid therefore represents the group of the hydroxycarboxylic acids, in particular of the aliphatic saturated and monounsaturated hydroxyl fatty acids which include 10 to 22 C atoms, for example ricinoleic acid (12-hydroxyoctadec-9-enoic acid).

Preferred among the abovementioned substances are the polyethoxylates, i.e. the substances obtained by conversion with ethylene oxide, and the poly(ethoxylate-co-propoxylates), that is to say the reaction products of the abovementioned substances with ethylene oxide and propylene oxide.

In preferred plant strengtheners according to the invention, component B comprises at least one nonionic surfactant selected from among group B.9, in particular at least one poly-$C_2$-$C_3$-alkoxylated castor oil, preferably one with a degree of alkoxylation in the range of from 10 to 100, in particular from 15 to 70, specifically from 20 to 60, specifically at least one castor oil ethoxylate, very specifically at least one castor oil ethoxylate with a degree of ethoxylation in the range of from 10 to 100, in particular from 15 to 70, specifically from 20 to 60, for example a castor oil ethoxylate with a degree of ethoxylation of 40. If appropriate, component B comprises one or more further nonionic surfactants from among groups B.1 to B.8. In particular, the nonionic surfactant selected from among group B.9 accounts for at least 50% by weight, in particular at least 80% by weight, of component B. Specifically, the surfactant from among group B.9 is the sole constituent of component B.

The plant strengtheners according to the invention comprise component B preferably in such an amount that the weight ratio of component A to component B is in the range of from 10:1 to 1:1, in particular in the range of from 3:1 to 1:1. Preferably, the plant strengtheners according to the invention comprise component B in a concentration of from 50 to 400 g/l, in particular from 100 to 300 g/l.

Component C of the plant strengtheners according to the invention is preferably among alkali metal borates, in particular sodium orthoborate or sodium metaborate, boric acid such as orthoboric acid or oligoboric acids with degrees of oligomerization of from 2 to 10, and boric esters, for example boric esters with $C_1$-$C_4$-alkanols such as methanol or ethanol, or boric, esters with $C_2$-$C_4$-aminoalkanols such as boroethanolamine (monoester of boric acid with ethanolamine: Cas No. 10377-81-8, EINECS number: 233-829-3). Especially preferably, component C comprises or is at least one substance selected among boric esters with $C_2$-$C_4$-aminoalkanols, in particular the mono- and diesters such as boroethanolamine.

The plant strengtheners according to the invention comprise component A and component C preferably in such an ratio that the proportion of component A to the boron content of component C, calculated as $B_2O_3$, is in the range of from 1:2 to 5:1, in particular in the range of from 3:4 to 4:1 by weight. The boron concentration in the compositions according to the invention, calculated as elemental boron, is preferably in the range of from 5 to 50 g/l, in particular from 10 to 40 g/l. Preferably, the composition comprises component C in a concentration of from 50 to 400 g/l.

Besides the abovementioned components A, B and C, the plant strengtheners according to the invention may also comprise one or more UV absorbers (hereinbelow component D). Preferred UV absorbers are those which are based on phenylpropanoids, such as cinnamic acid and cinnamic acid derivatives, i.e. compounds which include a cinnamic acid structural unit, but also coniferyl alcohol, safrole, umbelliferone and reservatrol. Preferred UV absorbers are cinnamic acid and cinnamic acid derivatives, in particular those in which the cinnamic acid or cinnamic acid derivative includes at least one methoxy group on the phenyl ring, which methoxy group is preferably arranged in the 3- or 4-position (so-called methoxycinnamic acid and methoxycinnamic acid derivatives). Suitable cinnamic acid derivatives or methoxycinnamic acid derivatives are mainly the $C_1$-$C_{20}$-alkyl esters, in particular the $C_4$-$C_{18}$-alkyl esters. Especially preferred UV absorbers are those which are described by formula D.1 hereinbelow, including their E and Z isomers:

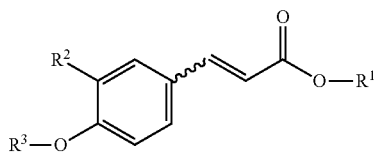

D.1

In formula D.1, $R^1$ represents hydrogen or $C_1$-$C_{20}$-alkyl, in particular $C_4$-$C_{18}$-alkyl; $R^2$ represents hydrogen, methoxy or hydroxyl and in particular hydrogen; $R^3$ represents hydrogen or methyl. Examples of suitable compounds of the formula D.1 are ferulic acid ($R^1$=$R^3$=hydrogen, $R^2$=methoxy), and 4-methoxycinnamic acid and its $C_4$-$C_{18}$-alkyl esters (compounds of the formula D.1 where $R^1$=$C_4$-$C_{18}$-alkyl, $R^2$=hydrogen, $R^3$=methyl), for example the isoamyl ester or the 2-ethylhexyl ester of 4-methoxycinnamic acid, and mixtures of these.

If desired, the plant strengtheners according to the invention comprise component D in a concentration of from 50 to 250 g/l.

The plant strengtheners according to the invention may be formulated as aqueous or nonaqueous products. In a preferred embodiment, plant strengtheners according to the invention are nonaqueous formulations, i.e. their water content amounts to not more than 100 g/l, in particular not more than 70 g/l, based on the total weight of the formulation. Any amounts of water result, as a rule, from the nonaqueous starting materials, such as boron component or solvent E.

In preferred developments, the plant strengtheners according to the invention comprise at least one polar organic solvent as component E, in addition to the abovementioned constituents A, B, C and, if appropriate, D.

Examples of such polar organic solvents are $C_2$-$C_6$-alkylene glycols such as ethylene glycol, propylene glycol and butanediol, glycerol, benzyl alcohol, dimethyl sulfoxide, hydroxy-$C_2$-$C_4$-alkyl esters of aliphatic $C_1$-$C_4$-carboxylic acids, in particular hydroxyethyl esters and hydroxypropyl esters of acetic acid or propionic acid, such as 2-hydroxyethyl acetate, 2-hydroxyethyl propionate, 2-hydroxypropyl acetate, 3-hydroxypropyl acetate, 2-hydroxypropyl propionate or 3-hydroxypropyl propionate, $C_1$-$C_4$-alkoxy-$C_2$-$C_4$-alkyl esters of aliphatic $C_1$-$C_4$-carboxylic acids, in particular methoxyethyl esters, ethoxyethyl esters, methoxypropyl esters and ethoxypropyl esters of acetic acid or propionic acid, such as 2-methoxyethyl acetate, 2-methoxyethyl propionate, 2-methoxypropyl acetate, 3-methoxypropyl acetate, 2-ethoxyethyl acetate, 2-ethoxyethyl propionate, 2-ethoxypropyl acetate or 3-ethoxypropyl acetate, $C_1$-$C_4$-alkyl esters of lactic acid such as methyl lactate and ethyl lactate and oligo-$C_2$-$C_4$-alkylene glycol esters of aliphatic $C_1$-$C_{10}$-carboxylic acids, in particular oligoethylene glycol esters and oligopropylene glycol esters of acetic acid, such as diethylene glycol monoacetate, dipropylene glycol monoacetate or triethylene glycol monoacetate.

If present, the total amount of polar organic solvents will, as a rule, account for at least 50 g/l and will preferably not exceed 500 g/l, in each case based on the total volume of the formulation. In particular, the total concentration of polar organic solvents amounts to 100 to 400 g/l.

It has proved to be advantageous for the invention if the formulation comprises dimethyl sulfoxide. Accordingly, a preferred group of embodiments of the invention relates to those plant strengtheners in which component E comprises dimethyl sulfoxide. In this group of the embodiments, dimethyl sulfoxide may be the sole polar organic solvent. Others which are suitable are mixtures of dimethyl sulfoxide with one or more polar organic solvents which differ therefrom. In these embodiments, the plant strengtheners according to the invention preferably comprise dimethyl sulfoxide in a concentration of from 50 to 450 g/l, in particular in a concentration of from 100 to 300 g/l.

In particular, the component comprises, besides dimethyl sulfoxide, at least one further polar organic solvent which is selected among the following groups: $C_2$-$C_6$-alkylene glycols, glycerol, benzyl alcohol, hydroxy-$C_2$-$C_4$-alkyl esters of aliphatic $C_1$-$C_4$-carboxylic acids, $C_1$-$C_4$-alkoxy-$C_2$-$C_4$-alkyl esters of aliphatic $C_1$-$C_4$-carboxylic acids, $C_1$-$C_4$-alkyl esters of lactic acid and oligo-$C_2$-$C_4$-alkylene glycol esters of aliphatic $C_1$-$C_{10}$-carboxylic acids, in particular among ethylene glycol, propylene glycol, glycerol, benzyl alcohol, hydroxyethyl esters and hydroxypropyl esters of acetic acid or propionic acid, methoxyethyl esters, ethoxyethyl esters, methoxypropyl esters and ethoxypropyl esters of acetic acid or propionic acid, methyl lactate, ethyl lactate and oligoethylene glycol esters and oligopropylene glycol esters of acetic acid. Preferably, the weight ratio of dimethyl sulfoxide to the at least one further polar organic solvent is in the range of from 5:1 to 1:5 and in particular in the range of from 3:1 to 1:3. In these embodiments, the plant strengtheners according to the invention comprise the further polar organic solvent preferably in a concentration of from 50 to 450 g/l, in particular in a concentration of from 100 to 300 g/l.

An especially preferred group of embodiments of the invention relates to those plant strengtheners in which component E comprises dimethyl sulfoxide and benzyl alcohol. In these especially preferred embodiments, the plant strengtheners according to the invention comprise the dimethyl sulfoxide preferably in a concentration of from 50 to 350 g/l, in particular in a concentration of from 100 to 300 g/l, and the benzyl alcohol in a concentration of from 50 to 350 g/l, in particular in a concentration of from 100 to 300 g/l. In addition, component E may also comprise one or more further organic polar solvents other than dimethyl sulfoxide and benzyl alcohol. If present, the concentration of these further solvents will not exceed preferably 200 g/l and is in particular in the range of from 20 to 200 g/l and in particular in the range of from 50 to 150 g/l. Preferred further organic polar solvents are mainly $C_2$-$C_6$-alkylene glycols, in particular ethylene glycol or propylene glycol, and glycerol.

Besides the abovementioned components, the plant strengtheners according to the invention may also comprise one or more further constituents as they are usually employed in plant treatment products. These include stabilizers, for example phenolic antioxidants such as tert.-butylhydroxytoluene (BHT) or tert.-butylhydroxyanisole (BHA), biocides and preservatives, for example salicylic acid and its salts, isothiazolones and ascorbic acid and its salts. Preferably, the total concentration of these agents will not exceed 50 g/l in total.

The plant strengtheners according to the invention may be prepared analogously to known processes of formulation technology. To this end, one will, as a rule, mix the components of the plant strengtheners according to the invention with each other, the order of the addition upon mixing being, in principle, arbitrary. Preferably, a procedure will be followed in which components A, B, C and, if appropriate, D and E are combined and stirred until a homogeneous mixture is obtained. Preferably, components A, B and, if appropriate, D will be combined first and C and, if appropriate, component D and C will be added thereto, it being preferred to incorporate component C as the last component into the formulation.

The invention also relates to the use of a plant strengthener as claimed in any of the preceding claims for increasing the tolerance of crop plants to stress events, in particular to chemically induced stress, cold-induced stress, drought-induced stress or light-induced stress.

For the use according to the invention, the plant strengtheners will be applied in a manner known per se, i.e. the plant or its environment will be treated with a plant strengthener according to the invention.

The plant strengtheners according to the invention are suitable for application to all higher plants and also independently of the growing region, the climate or the soil. Depending on the location and the plant part of the application, they can be applied using equipment which is known per se and conventionally employed in agricultural practice, for example preferably as an aqueous dilution, i.e. as a spray solution or spray mixture.

It is preferred to treat the plants, in particular the aerial plant parts for example all of the aerial plant parts or individual plant parts such as foliage, shoots, buds, inflorescences or fruits.

Preferably, the treatment is carried out before a stress event to be expected, the treatment being carried out in particular at a point in time which is a few hours up to several days, in particular 12 h to 120 h, specifically 24 h to 72 h before a stress event to be expected, for example a period of heat or drought to be expected or a planned application of a plant protectant which is known to potentially display phytotoxic side effects. Naturally, a purely prophylactic treatment without a stress event to be expected may also be carried out. Likewise, a treatment may be carried out during a stress event, in particular as a follow-up treatment following a first treatment which took place before the stress event.

When used in accordance with the invention, the plant strengthener according to the invention is preferably applied in the form of an aqueous dilution, where, depending on the further constituents, component A is present in emulsified or suspended form in these aqueous dilutions.

Regarding the amount of component A which is used in accordance with the invention, it should be remembered that unduly high concentrations of vitamin E compounds may cause phytotoxic effects. The concentration of component A, or the amount of water for dilution, is therefore preferably chosen such that the concentration of component A in the dilution can be expected not to cause any substantial phytotoxic effects. Preferably the concentration of component A in the aqueous dilution is in the range of from 0.001 to 5% by weight, in particular 0.01 to 1% by weight and specifically 0.05 to 0.25% by weight, based on the aqueous dilution. The concentration which is preferred in accordance with the invention, of surfactant and of the remaining components, then also results from the preferred ratio of component A to component B. Preferably, the plant strengthener is applied in such an amount that the application rate of component A is from 100 to 1 000 g/ha.

The plant strengtheners according to the invention can be applied alone or else in combination with one or more plant protectants which comprise one or more active substances which are suitable for plant protection and/or as growth regulator. To this end, the composition according to the invention, in the form of the formulation according to the invention, may be admixed to one or more other plant protectants which comprise such active substances and which may likewise be present in the form of a concentrate, and the mixture can then be applied, if appropriate after previously having been suitably diluted.

The plant strengtheners according to the invention can be applied in combination with one or more other plant protectants simultaneously with the latter, for example in the form of a mixture, or is preferably applied before the other plant protectants are applied, for example 1 to 2 days before the application of the other agrochemicals. The plant strengthener according to the invention, if appropriate together with another plant protectant, can be applied to the entire plant, the stem, the roots, the seeds, the fruits, the shoots and/or the soil where growth takes place, but application to the leaves is preferred.

The plant strengtheners according to the invention furthermore also have outstanding storage stability, and the active substance, i.e. component A, is stable in the use form, for example the spray mixture, for at least as long as a sufficient amount of the active substance has been taken up by the plant.

According to the invention there is therefore provided a composition with which phytotoxicity caused by agrochemicals and/or environmental toxins and also by unfavorable climatic conditions (for example heat, frost) can be inhibited or at least greatly reduced. In this manner, the quality of the plants and of their products may be enhanced, and the performance of crop plants may be increased and their yield can be enhanced.

The examples which follow are intended to illustrate the invention:

The following starting materials were used:

DL-α-Tocopherol from S. Goldmann GmbH und Co KG, Bielelfeld (oil, concentration 96%).

Emulsifier: Ethoxylated castor oil (40 EO units) (Marlowet® R40 from Sasol Olefins and Surfactants GmbH, Hamburg Boroethanolamine (10% by weight of boron): COMPO EXPERT, Krefeld;

UV filter 1: 2-Ethylhexyl 4-methoxycinnamate (Neoheliopan AV>98%) from Cosnaderm Chemische Rohstoffe, Ladenburg;

UV filter 2: Ferulic acid, concentration>98%, from Carl Roth GmbH und Co KG, Karlsruhe.

The following formulations F1, F2, FV1 and FV2 were prepared by mixing the constituents specified in table 1. The data specified in table 1 are the relative amounts of the constituents in parts by weight. The constituents were mixed in the stated order:

Formulation FV1: DL-α-tocopherol, emulsifier, dimethyl sulfoxide, benzyl alcohol, ethylene glycol.

Formulations FV2: DL-α-tocopherol, emulsifier, dimethyl sulfoxide, benzyl alcohol, UV filter 1, UV filter 2;

Formulation F1: Addition of boroethanolamine to formulation FV1.

Formulation F2: Addition of boroethanolamine to formulation FV2.

TABLE 1

| Component | FV1 | F1 | FV2 | F2 |
|---|---|---|---|---|
| DL-α-Tocopherol | 200 | 200 | 210 | 210 |
| Emulsifier | 140 | 140 | 140 | 140 |
| Dimethyl sulfoxide | 200 | 200 | 200 | 200 |
| Benzyl alcohol | 150 | 150 | 150 | 150 |
| Ethylene glycol | 90 | 90 | — | — |
| Boroethanolamine | — | 210 | — | 210 |
| UV filter 1 | — | — | 40 | 40 |
| UV filter 2 | — | — | 40 | 40 |

Study of the Effect Against Stress Events:

For the following studies, tocopherol-comprising formulations were diluted with water to give a tocopherol concentration of 0.25% by weight.

Boroethanolamine was diluted with water to give a concentration of 0.25% by weight.

Freshly severed branches with 20 to 50 inflorescences (inflorescence stage BBCH 60-69) were used for studying the protection of inflorescences. The twigs were sprayed to runoff point with the aqueous dilution of the respective formulation, using a hand-held sprayer.

To study the protection of young plants, seedlings of tomato or bell pepper plants were planted in plant compost and grown to a plant height of approximately 15 to 25 cm with regular irrigation and nutrient supply. The plants were sprayed to runoff point with the aqueous dilution of the respective formulation, using a hand-held sprayer.

For the field experiments, the formulations were diluted with tap water in an amount of 100 l per kg of formulation. The plants were sprayed with the aqueous dilution with the aid of a commercially available plant protection sprayer at an application rate of 0.25 kg tocopherol/ha.

Activity on Frost Protection

The tests of the formulations in respect of their frost protectant activity were carried out under controlled conditions in frost chambers with fruit-tree inflorescences (apple (variety Elstar), severed branches, sweet cherry (variety Hedelfinger), severed branches).

The fruit trees were treated 24 hours before the frost event by spraying the inflorescences with the dilute formulation.

(a) Control (untreated),
(b) Treatment with formulation FV1 (0.25 g/l tocopherol),
(c) Treatment with formulation F1 (0.25 g/l tocopherol)+ 0.25 g/l boroethanolamine).

The branches were severed from the plant shortly before the test and then exposed to a temperature of −2° C. for a defined period (4 hours). On the following day, the relative number of the inflorescences with frost damage was determined visually. Damage was considered to be browning of the floral tissue (pedicel and ovaries).

100% of untreated cherry inflorescences were damaged, whereas 73% of the inflorescences treated with the comparative formulation FV1 and 65% of the inflorescences treated with formulation F1 were damaged.

75% of untreated apple inflorescences were damaged, whereas 80% of the inflorescences treated with the comparative formulation FV1 and 72% of the inflorescences treated with formulation F1 were damaged.

The treatment with the dilute aqueous boroethanolamine preparation (0.25 kg/ha) revealed no significant change over the control.

The compositions for fruit-tree blossom and for the protection of young plants at various locations in the field may be studied in the same manner.

Effect on Protection Against Sun-Scorch a) Greenhouse Experiments:

The tests of the formulations in respect of their sun-protection activity were carried out on fruits (apple) or on plants under controlled conditions. The fruits or the plants were briefly (1 to 2 hours) exposed to a defined UVA/UVB-ray dose. Thereafter, the radiation damage (discolorations of the fruits' skins, discoloration of the leaf tissue, overall habit of the plant) were rated from 0 to 3, using the following scale. The following formulations were employed: Treatments: (a) control (no test product), (b) formulation FV2 without addition of boroethanolamine, (c) Formulation F2 with addition of boroethanolamine, (d) boroethanolamine.

0 no damage to fruit skin/plant
1 slight damage to fruit skin/plant
2 medium damage to fruit skin/plant
3 severe damage to fruit skin/plant b) Field Experiments on Apples The study was carried out in an apple plantation in South Africa (Somerset-West region) in February.

To this end, apple trees cv. "Granny Smith" were sprayed with an aqueous dilution of formulation F2 or formulation FV2 8 days before the harvest in two adjacent plots, in parallel experiments. The controls used were in each case untreated trees of the same plot.

To determine the damage, in each case approximately 30 fruits were harvested from each tree of the treated trees and of the untreated trees and then observed. The proportion of damaged fruits of the treated trees and of the untreated trees of the respective experiment was determined, and the percentage reduction in damage was determined on this basis. Damage was considered to be reddish and brownish discolorations of the fruit skin.

In the experiment with formulation FV2 (without boroethanolamine), a 20% reduction in damage was achieved. In the experiment with formulation F2 a 47% reduction in damage was achieved.

The treatment with dilute aqueous boroethanolamine preparation (0.25 kg/ha) revealed no significant change over the control.

c) Field Experiments on Tangerines (Satsumas)

The study was carried out in a fruit plantation in South Africa (Western Cape region, Simondium) in February.

To this end, tangerine trees cv. "satsuma" were sprayed with an aqueous dilution of formulation F2 or formulation FV2 6 days before the harvest in two adjacent plots, in parallel experiments. The controls used were in each case untreated trees of the same plot.

To determine the damage, in each case approximately 30 fruits were harvested from each tree of the treated trees and of the untreated trees and then observed. The proportion of damaged fruits of the treated trees and of the untreated trees of the respective experiment was determined, and the percentage reduction in damage was determined on this basis. Damage was considered to be yellowish discolorations of the green fruit skin.

In the experiment with formulation FV2 (without boroethanolamine), no reduction in damage was achieved. In the experiment with formulation F2 a 66% reduction in damage was achieved.

The treatment with dilute aqueous boroethanolamine preparation (0.25 kg/ha) revealed no significant change over the control.

We claim:

1. A plant strengthener in the form of a formulation comprising
   a) at least one tocopherol or a derivative of a tocopherol (component A);
   b) at least one nonionic emulsifier (component B);
   c) at least one water-soluble boron compound (component C), which is selected from the group consisting of boric esters with $C_2$-$C_4$-aminoalkanols; and
   e) polar organic solvents (component E), where the polar organic solvents are a mixture of dimethyl sulfoxide and at least one further polar organic solvent which is selected from the group consisting of $C_2$-$C_6$-alkylene glycols, glycerol, benzyl alcohol, hydroxy $C_2$-$C_4$-alkyl esters of aliphatic $C_1$-$C_4$-carboxylic acids, $C_1$-$C_4$-alkoxy-$C_2$-$C_4$-alkyl esters of aliphatic $C_1$-$C_4$-carboxylic acids, $C_1$-$C_4$-alkyl esters of lactic acid and oligo-$C_2$-$C_4$-alkylene glycol esters of aliphatic $C_1$-$C_{10}$-carboxylic acids;
where the formulation contains component A and component C in such a weight ratio that the proportion of component A to the boron content of component C, calculated as $B_2O_3$, is in the range of from 1:2 to 5:1.

2. The plant strengthener as claimed in claim 1, comprising α-tocopherol.

3. The plant strengthener as claimed in claim 1, wherein component B is selected from the group consisting of poly-$C_2$-$C_3$-alkoxylated $C_3$-$C_{18}$-alkylphenols, poly-$C_2$-$C_3$-alkoxylated $C_{10}$-$C_{22}$-fatty alcohols, poly-$C_2$-$C_3$-alkoxylated $C_{10}$-$C_{22}$-fatty acid esters, copolymers of propylene oxide/ethylene oxide, sucroglycerides, polyethoxylated $C_{10}$-$C_{22}$-fatty acid esters of sorbitan, polyethoxylated lanolin alcohols, $C_8$-$C_{16}$-alkylpolyglucosides, poly-$C_2$-$C_3$-alkoxylated triglycerides of aliphatic $C_{10}$-$C_{22}$-hydroxycarboxylic acids and their mixtures.

4. The plant strengthener as claimed in claim 3, wherein component B comprises at least one castor oil ethoxylate.

5. The plant strengthener as claimed in claim 1, wherein the weight ratio of component A to component B is in the range of from 1:1 to 10:1 by weight.

6. The plant strengthener as claimed in claim 1, further comprising an organic UV absorber as component D.

7. The plant strengthener as claimed in claim 1, comprising components A, B, C and E in the following concentrations:
   a) 50 to 500 g/l of component A;
   b) 50 to 400 g/l of component B;
   c) 5 to 50 g/l of component C, calculated as elemental boron; and
   e) 50 to 500 g/l of component E,
      wherein the concentrations are based on the total volume of the plant strengthener.

8. A method for increasing the tolerance of crop plants to stress events comprising treating a crop plant or its environment with a plant strengthener of claim 1.

9. The method of claim 8, wherein the plant strengthener is applied before the stress event to be expected.

10. A method for the treatment of plants, in which the plant or its environment is treated with a plant strengthener as claimed in claim 1.

11. The plant strengthener as claimed in claim 1, wherein the weight ratio of component A to component B is in the range of from 1:1 to 3:1 by weight.

12. The plant strengthener as claimed in claim 1, comprising component A and component C in such a weight ratio that the proportion of component A to the boron content of component C, calculated as $B_2O_3$, is in the range of from 3:4 to 4:1 by weight.

13. The method of claim 8, wherein the stress event is chemically induced stress, cold-induced stress, drought-induced stress or light-induced stress.

14. The plant strengthener as claimed in claim 1, where component C is boron ethanolamine.

15. The plant strengthener as claimed in claim 6, comprising components A, B, C, D and E in the following concentrations:
   a) 50 to 500 g/l of component A;
   b) 50 to 400 g/l of component B;
   c) 5 to 50 g/l of component C, calculated as elemental boron;
   d) 50 to 250 g/l of component D; and
   e) 100 to 400 g/l of component E,
      wherein the concentrations are based on the total volume of the plant strengthener.

16. The plant strengthener as claimed in claim 1, comprising components A, B, C and E in the following concentrations:

a) 50 to 500 g/l of component A;
b) 50 to 400 g/l of component B;
c) 5 to 50 g/l of component C, calculated as elemental boron; and
e) 50 to 500 g/l of component E,
wherein the weight ratio of component A to component B is in the range of from 1:1 to 3:1 by weight, and wherein the concentrations are based on the total volume of the plant strengthener.

17. The plant strengthener as claimed in claim 16, comprising component A and component C in such a weight ratio that the proportion of component A to the boron content of component C, calculated as $B_2O_3$, is in the range of from 3:4 to 4:1 by weight.

18. The plant strengthener as claimed in claim 6, comprising components A, B, C, D and E in the following concentrations:

a) 50 to 500 g/l of component A;
b) 50 to 400 g/l of component B;
c) 5 to 50 g/l of component C, calculated as elemental boron;
d) 50 to 250 g/l of component D; and
e) 100 to 400 g/l of component E,
wherein the weight ratio of component A to component B is in the range of from 1:1 to 3:1 by weight, and wherein the concentrations are based on the total volume of the plant strengthener.

19. The plant strengthener as claimed in claim 18, comprising component A and component C in such a weight ratio that the proportion of component A to the boron content of component C, calculated as $B_2O_3$, is in the range of from 3:4 to 4:1 by weight.

* * * * *